United States Patent [19]

Strong

[11] Patent Number: 5,380,911
[45] Date of Patent: Jan. 10, 1995

[54] PROCESS FOR THE MANUFACTURE OF CYCLOPROPYLNITRILE

[75] Inventor: Henry L. Strong, Somerset, N.J.

[73] Assignee: American Cyanamid Company, Wayne, N.J.

[21] Appl. No.: 161,111

[22] Filed: Dec. 2, 1993

[51] Int. Cl.$^6$ .................. C07C 253/30; C07C 255/45
[52] U.S. Cl. .................................................. 558/434
[58] Field of Search ........................................ 558/434

[56] References Cited

U.S. PATENT DOCUMENTS

| | | | |
|---|---|---|---|
| 3,843,709 | 10/1974 | Bacha et al. | 558/434 |
| 3,847,985 | 11/1974 | Linder et al. | 558/434 X |
| 3,853,942 | 12/1974 | Sury et al. | 558/434 |
| 3,974,199 | 8/1976 | Plonka et al. | 558/434 |
| 4,205,009 | 5/1980 | Onore et al. | 558/434 |
| 4,622,065 | 11/1986 | Van Gemert | 544/211 X |
| 5,009,699 | 4/1991 | Brady et al. | 544/321 X |
| 5,107,023 | 4/1992 | Brady et al. | 564/305 |

FOREIGN PATENT DOCUMENTS

| | | | |
|---|---|---|---|
| 624663 | 8/1981 | Switzerland | 558/434 |
| 1570319 | 6/1980 | United Kingdom | 558/434 |

*Primary Examiner*—Joseph Paul Brust
*Attorney, Agent, or Firm*—Peggy A. Climenson

[57] ABSTRACT

An improved manufacturing procedure for the preparation and isolation of cyclopropylnitrile is provided. 4-Halobutyronitrile is reacted with an alkali metal base in the presence of an aprotic polar solvent, an inorganic salt and a catalytic amount of water at an elevated temperature. The reaction product cyclopropylnitrile is isolated by azeotropic distillation.

18 Claims, No Drawings

PROCESS FOR THE MANUFACTURE OF CYCLOPROPYLNITRILE

BACKGROUND OF INVENTION

Cyclopropylnitrile is a vital raw material in the manufacture of herbicidal agents. It is particularly useful in the manufacture of herbicidally potent, yet environmentally benign 1-(o-cyclopropylcarbonyl)-phenylsulfamoyl urea derivatives. The preparation of cyclopropylnitrile from 4-chlorobutyronitrile is described in U.S. Pat. No. 3,843,709. However, when this preparation is applied to a manufacturing scale, an unstirrable mass forms causing decreased reaction yield, broken or damaged equipment and problematic product isolation.

Therefore it is an object of this invention to provide an improved process for the manufacture of cyclopropylnitrile which is suitable for large scale production with increased isolated product yield.

It is another object of this invention to provide an efficient and effective method of isolation of cyclopropylnitrile in high purity and with essentially no water content.

It is a further object of this invention to provide a convenient and economic source of essential starting material in the production of herbicidal sulfamoyl urea derivatives.

SUMMARY OF INVENTION

The present invention provides an improved process for the commercial scale manufacture of cyclopropylnitrile which comprises reacting 4-halobutyronitrile with an alkali metal base in the presence of an aprotic polar solvent, an inorganic salt and a catalytic amount of water at an elevated temperature.

The present invention also provides a simple and direct isolation method comprising neutralization of the crude reaction mixture, dilution of the neutralized reaction mixture with water, and azeotropic distillation thereof to give the product cyclopropylnitrile in high purity and essentially no water content.

The essentially anhydrous, pure cyclopropylnitrile is highly useful as a starting material in the production of crop-selective sulfamoyl urea herbicides.

DETAILED DESCRIPTION OF THE INVENTION

Herbicidal agents and in particular 1-(o-cyclopropylcarbonyl)phenylsulfamoyl urea derivatives are prepared using cyclopropylnitrile as the basic starting material. The sulfamoyl urea derivatives are highly valued, potent, environmentally benign herbicides which demonstrate cereal crop tolerance. It has now been found that cyclopropylnitrile can be prepared on a commercial manufacturing scale without the formation of an unstirrable mass and accompanying equipment damage or breakage and decreased product yield by reacting 4-halobutyronitrile with an alkali metal base in the presence of an aprotic polar solvent, an inorganic salt and a catalytic amount of water at a temperature of about 50°–100° C. The preparation is shown in flow diagram I wherein X is halogen, M is an alkali metal and R is hydrogen or $C_1$–$C_6$alkyl.

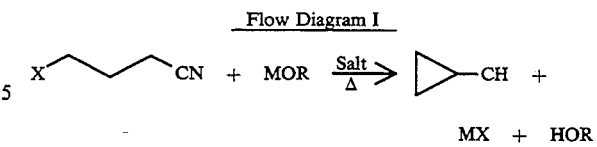

Flow Diagram I

Methods available in the art to prepare cyclopropylnitrile, upon scale-up, give the formation of an unstirrable mass. The inability to stir or agitate a reaction mixture results in incomplete reaction, hazardous reaction conditions and damaged or broken equipment. Surprisingly, it has been found that the addition of at least 0.25 mole, preferably about 0.4 to 1.5 mole and more preferably about 0.5 to 1.0 mole of an inorganic salt eliminates the formation of an unstirrable mass thus preventing agitation problems, poor yields and a broken or damaged agitator. Advantageously, it has been found that the addition of a catalytic amount of water to the reaction mixture is critical to the initiation of the reaction. Predictable and reproducable reaction initiation prevents the potential hazard of large scale run-away reaction rates and sudden uncontrollable exotherms.

In general, the reaction rate increases as the temperature increases, however it has now been found that under large scale conditions, reaction temperatures greater than about 110° C. give mainly amide side-product formation and little or no cyclopropylnitrile product. Elevated temperatures of about 50°–100° C., preferably about 60°–90° C. are suitable in the inventive process.

Aprotic polar solvents suitable for use in the inventive process are sulfoxides, sulfones, carboxylic acid amides, pyrrolidones and the like. Sulfoxides and carboxylic acid amides are preferred, dimethylsulfoxide and dimethyl formamide are more preferred and dimethylsulfoxide is most preferred.

Alkali metal bases useful in the process of the invention are any alkali metal hydroxides or alkoxides or mixtures thereof. Preferable alkali metal bases are monovalent bases such as NaOR, KOR or LiOR, more preferred are the hydroxides of sodium or potassium and most preferred is NaOH. Stoichiometric amounts of the alkali metal base may be used in the process of the invention. In a preferred embodiment of the invention, the alkali metal base is added to the reaction mixture incrementally over a period of time.

Inorganic salts suitable for use in the present invention are metal halides, metal sulfates or metal carbonates, preferably metal halides such as sodium halide or potassium halide, more preferably sodium halide and most preferably sodium chloride.

The product cyclopropylnitrile, in order to be suitable for use in manufacturing 1-(o-cyclopropylcarbonyl)phenylsulfamyl urea derivatives, must be essentially free of water and minor components. It has now been found that highly pure and essentially anhydrous cyclopropylnitrile product can be isolated directly from the crude reaction mixture by direct azeotropic distillation thus avoiding the use of large amounts of extraction solvents and tedious and costly fraction distillation procedures. Upon completion of the reaction, the reaction mixture is cooled to about room temperature, neutralized to a pH range of about 4.0–9.0, preferably about 6–8, to avoid amide by-product formation, diluted with water to aide the azeotropic removal of the cyclopropylnitrile, and azeotropically distilled using a Dean Stark trap to give high purity, essentially anhydrous product cyclopropylnitrile. Advantageously, this procedure allows the isolation of pure cyclopropylnitrile on a manufacturing scale without the use and handling of extraction solvents and without the need for costly fraction distillation columns.

For a more clear understanding of the invention, specific examples thereof are set forth below. These examples are merely illustrative and are not to be understood as limiting the scope and underlying principles of the invention in any way.

The term GLC designates gas liquid chromatography.

EXAMPLE 1

Preparation of cyclopropylnitrile (2 molar scale)

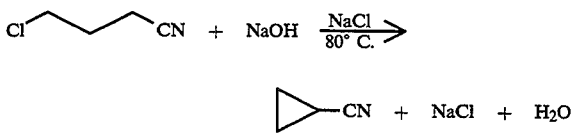

A stirred mixture of 4-chlorobutyronitrile (213.4 g, 2.0 mole), sodium chloride (58.0 g, 0.5 mole) and 2.0 g of water in 200 g of dimethylsulfoxide is heated to 80° C., treated with ground solid sodium hydroxide (88 g, 2.2 mole) over a 3 hour period and held at 80° C. for about 1 additional hour. The reaction mixture is cooled to room temperature neutralized to about pH6.8 with concentrated HCl (37% aqueous solution), diluted with 200 ml water (readjusted pH to 6.8 with 37% HCl) and azeotropically distilled with a Dean Stark trap to remove the cyclopropylnitrile/water azeotrope. The aqueous layer is continuously returned to the distillation pot to give the initial product as the distillate cyclopropylnitrile, 133.5 g. A 121.5 g sample of this cyclopropylnitrile is azeotropically distilled using a Dean Stark trap (to remove water) and continuous return of the organic layer to give the final product cyclopropylnitrile, 106.6. g, 87.8% yield, 98% pure by GLC analysis and 0.04% H$_2$O by Karl Fischer titration.

EXAMPLE 2

Preparation of cyclopropylnitrile (30 molar scale)

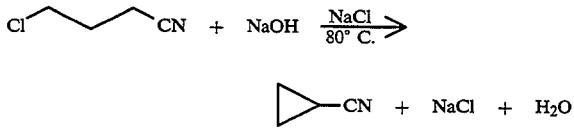

A stirred mixture of 4-chlorobutyronitrile (3.17kg, 30 mole), sodium chloride (0.87 kg, 15 mole) and 0.03kg water in 3.0kg of dimethylsulfoxide is heated to 80° C., treated with NaOH pellets (1.24 kg, 30.9 mole) over a 2 hour period and held at 80° C. for about 1 additional hour. (Another 0.012 kg of NaOH was added during the hold period. ) The reaction mixture is cooled to room temperature, neutralized to about pH 6.8–7.0, diluted with 3.0 L of water (readjusted pH to about 7.0) and azeotropically distilled with a Dean Stark trap to remove the cyclopropylnitrile/water azeotrope. The aqueous layer is continuously returned to the distillation pot to give the initial product cyclopropylnitrile distillate, 1.811 kg. A 1.72 kg sample of this cyclopropylnitrile is azeotropically distilled using a Dean Stark trap (to remove water) and continuous return of the organic layer to give the final product cyclopropylnitrile, 1.63 kg, 85% yield, 97.1% pure by GLC analysis and 0.28% H$_2$O by Karl Fischer titration.

EXAMPLE 3

Preparation of cyclopropylnitrile (Plant scale)

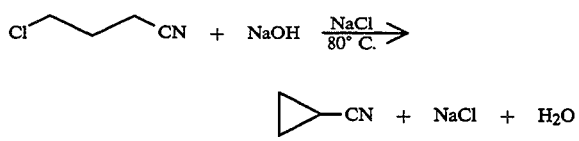

A)

Using essentially the same procedure described in Examples 1 and 2, cyclopropylnitrile is prepared on a 111kg scale (1.071 hole) in a pilot plant using 100 gallon and 500 gallon glass-lined reactors to give the initial cyclopropylnitrile product distillate, 59.3kg, 82.48% yield, 95.3% purity and 4.4% water content. This cyclopropylnitrile distillate is combined with another pilot plant batch and azeotropically dried as described in Examples 1 and 2 to give the final cyclopropylnitrile product, 95.1% recovery, 98.3% pure and 0.4% water content.

B)

Using the essentially the same procedure described above, cyclopropylnitrile is prepared on a plant scale of 1,021 kg(9.86 kmole), using a 2,000 gallon reactor to give the initial cyclopropylnitrile distillate, 592 kg, 89.5% yield, 95.2% pure and 4.4% water content. This product is combined with another plant run and azeotropically distilled to give the final cyclopropylnitrile product, 95.5% recovery, 96.4% pure and 0.4% water content.

EXAMPLES 4–8

Comparative preparation of cyclopropylnitrile
General Procedure

A stirred mixture of 4-chlorobutyronitrile and NaOH in dimethylsulfoxide, with and without NaCl and with and without a catalytic amount of water, is heated to 80° C. and stirring observations are made and recorded in Table I.

As can be seen from Table I, the absence of the addition of NaCl to the reaction mixture leads to an unstirrable mass and the absence of a catalytic amount of water may induce hazardous reaction conditions wherein the reaction rate is uncontrollable and large exotherms occur. When the stirring is poor or completely stopped, the reaction remains incomplete and product yields and purity are diminished.

TABLE I

| Example | 4-CBN[1] moles | NaOH moles | Water moles | NaCl moles | DMSO grams | Stirring |
|---|---|---|---|---|---|---|
| 4 | 1.0 | 1.1 | 0.0 | 0.0 | 200.0 | Poor[2] |
| 5 | 1.0 | 1.1 | 0.0 | 1.0 | 200.0 | Good |
| 6 | 2.0 | 2.0 | 0.1 | 1.0 | 200.0 | Good |
| 7 | 6.0 | 6.6 | 0.05 | 3.0 | 600.0 | Good |
| 8 | 1.0 | 1.1 | 0.0 | 0.5 | 200.0 | Good[3] |

[1]Chlorobutyronitrile
[2]Stirring completely impeded by reaction mass
[3]Hang-fire conditions (delayed reaction initiation followed by uncontrolled rate of reaction, temperature overshot)

I claim:

1. An improved process for the manufacture of cyclopropylnitrile which comprises mixing 4-halobutyronitrile, at least 0.25 moles of an inorganic salt and a catalytic amount of water in the presence of an aprotic polar solvent at an elevated temperature of about 50°–100° C. and reacting the mixture with an alkali metal base at the elevated temperature; wherein the inorganic salt is a metal halide, a metal sulfate or a metal carbonate and the metal is Na, K or Li.

2. The process according to claim 1 wherein the alkali metal base is MOR wherein M is Na, K or Li and R is hydrogen or $C_1$–$C_6$ alkyl.

3. The process according to claim 2 wherein M is Na and R is hydrogen.

4. The process according to claim 1 wherein about 0.4 to 1.5 mole of the inorganic salt is added.

5. The process according to claim 4 wherein about 0.5 to 1.0 mole of the inorganic salt is added.

6. The process according to claim 1 wherein the aprotic polar solvent is a sulfoxide or a carboxylic acid amide.

7. The process according to claim 6 wherein the solvent is a sulfoxide.

8. The process according to claim 7 wherein the solvent is dimethylsulfoxide.

9. The process according to claim 1 wherein the metal halide is sodium halide or potassium halide.

10. The process according to claim 9 wherein the metal halide is sodium chloride or potassium chloride.

11. The process according to claim 8 wherein the inorganic salt is sodium chloride.

12. The process according to claim 1 wherein the temperature is about 60°–90° C.

13. The process according to claim 12 wherein the alkali metal base is sodium hydroxide, the aprotic polar solvent is dimethylsulfoxide and the inorganic salt is sodium chloride.

14. The process according to claim 1 which further comprises (a) cooling the reaction temperature to room temperature when the reaction is complete, (b) neutralizing the cooled completed reaction, (c) diluting the neutralized reaction with water and (d) isolating the reaction product cyclopropylnitrile by azeotropic distillation.

15. The process according to claim 14 wherein the neutralized diluted reaction has a pH of about 4–9.

16. The process according to claim 15 wherein the pH is about 7–8.

17. The process according to claim 14 wherein the azeotropic distillation is conducted with a Dean Stark trap with continuous return of the aqueous layer.

18. The process according to claim 14 wherein the product cyclopropylnitrile is azeotropically distilled to an essentially anhydrous condition.

* * * * *